June 18, 1940. M. SAMTMANN Plant Pat. 402
ROSE
Filed Feb. 7, 1940
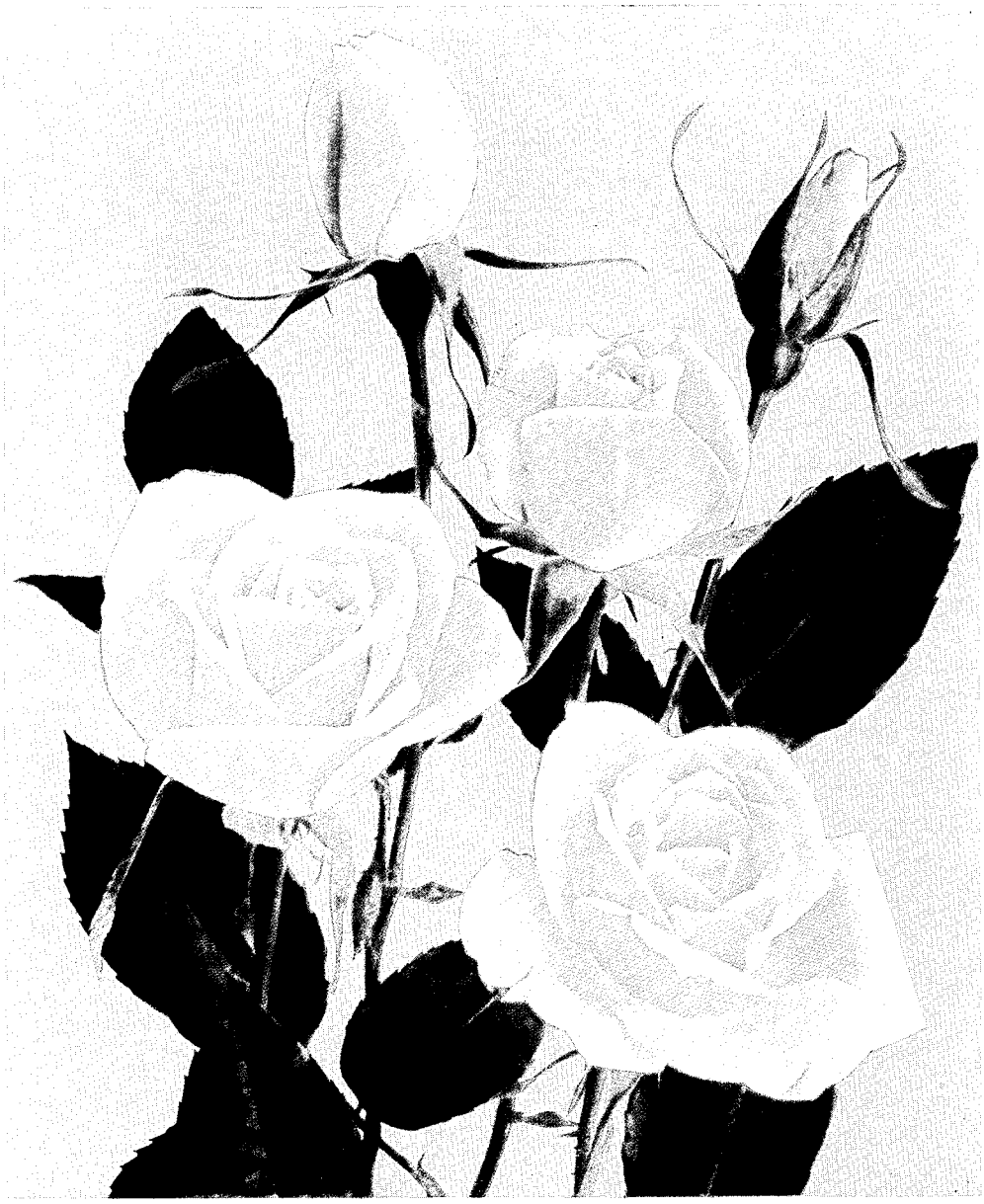
INVENTOR
Martin Samtmann
By Orville M Kile
Plant Patent Agt.

Patented June 18, 1940

Plant Pat. 402

UNITED STATES PATENT OFFICE

402

ROSE

Martin Samtmann, Wyndmoor, Pa.

Application February 7, 1940, Serial No. 317,751

1 Claim. (Cl. 47—61)

The present invention relates to a new and improved variety of hybrid tea roses, its coloring and other desirable features comprising its novelty.

My new variety originated as a bud sport on a plant of the Mrs. Franklin D. Roosevelt growing in my greenhouse. Immediately upon discovering this sport I began asexual reproduction by means of budding and have now built up considerable stock. The distinctive characteristics of the new variety have proved to be constant throughout this asexual reproduction.

In general, the growth and foliage characteristics of the parent variety are found in my new variety. The principal differences between the two varieties lie in the shape and color of the bud and the color of the blossom. The bud of the parent variety is long and slender, while my bud is broad at the base and pointed at the tip. And of course the color is in an entirely different range, the parent variety being a clear yellow.

Also outstanding among the features of this new variety are the slow and even opening of the bud, the exceedingly good lasting quality of the flower after being cut, and the dark, leathery foliage. These features combine to make this rose variety particularly adapted to shipping over considerable distances.

The distinctive color is extraordinarily rich and brilliant and is very difficult to describe because no color plates showing its true colors are available in the standard color guides. Reference is made to Ridgway's Color Standards and Nomenclature but exact designations are impossible in many instances.

The accompanying illustration shows several specimen blossoms of this variety in the bud stage and in the partially open stage, in as nearly their true colors as it is possible for the artist to depict them. It will be noted that as the buds open the color begins to change to a lighter tone, this change continuing throughout the opening process. When the full-blown stage is reached a much greater amount of the yellow and orange tones is shown, due partially to the actual lightening of the colors and partially to the fact that more of the lighter inner surface of the petals is then visible.

Following is a detailed description of this new variety.

*The plant*

Growth: Upright bush; vigorous; very similar to growth of its parent.

Blooming habit: Continuous bloomer; flowers occur singly on long, strong stems.

Stems: Oil Green (Plate V); long; very strong; straight; beset with many thorns.

Thorns: Many; irregularly placed; downward-pointing; slightly hooked; very sharp, long points; broad base; usually with light tinge of Corinthian Pink (Plate XXVII) which is more intense next the stem. Usually two or three small white thorns with very sharp points are found on the under side of the rachis. Numerous sharp, white spines or needles are found on the peduncle.

Foliage: Abundant.

*Leaves.*—Compound, with 3 to 7 leaflets, usually 5. *Leaflets*—lateral leaflets are practically sessile to rachis. *Shape*—ovate to lanceolate, with rounded base and tip acute to acuminate. Unusually long and relatively narrow. Edge coarsely and regularly serrated. *Size*—large, terminal leaflet measures 3 to 3½ inches long by 1½ to 2 inches wide. Color—approximately Dark Cress Green (Plate XXXI) on upper surface; Light Elm Green (Plate XVII) on under surface. *Texture*—leathery. *Appearance*—upper side glossy; veins prominent. Under side dull.

Rachis: Medium size; grooved on upper surface; usually with two or three sharp white thorns on under side. Color same as that of stems.

Stipules: Medium in length and width; smooth; clinging except for long, straight, sharp points.

*The blossom*

Bud:

*Size.*—Medium, measuring 1¾ inches long just before beginning to spread.

*Form.*—Pointed, with large base. Opens to modified urn-shape.

*Color.*—There is no color in Ridgway's Color Standards which approaches the color of this bud. The nearest is a cross between Scarlet (Plate I) and Coral Red (Plate XIII). The common name which I would apply is "a beautiful shade of burnt orange." This color is rather evenly spread except that there is a large aiglet of yellow which is a little more brilliant than Light Cadmium (Plate IV). A hair line of this yellow color also extends up the midrib and outlines the edges of the outer petals.

*Opening.*—Very slow and perfect.

*Peduncle.*—Long; stiff; covered with sharp, white spines; slightly lighter in color tone than the stems.

*Sepals.*—Very long, extending beyond the bud. Tips of one or two of the sepals are slightly foliaceous. Upon opening, the sepals extend at right angles to peduncle. When the flower is fully open, they turn backward somewhat but never cling against the peduncle. The outside surface is the same color as the stem; the inside surface is hairy and Light Cress Green (Plate XXXI) except for the foliaceous tips which are the same color as the foliage.

*Calyx.*—Large; same color as the peduncle.

Blossom:

*Size.*—Large, attaining a spread of 4 to 4½ inches.

*Petalage.*—Double, with 25 to 40 petals. Only a very few petaloids are present.

*Form.*—High-centered at first; slowly changes to deep cup-shape which is retained. Stamens and pistils are never visible until the later stages of maturity of the blossom.

*Petals.*—*Size*—outer petals are 2 inches by 2¼ inches, the horizontal measurement being the greater. *Shape*—almost round. Usually has a single point at center of tip. Petals toward center of flower are relatively narrower. *Arrangement*—imbricated. *Texture*—substantial. *Persistence*—clinging. *Fragrance*—moderate and pleasing. *Color*—the color of this rose changes greatly from one stage of maturity to another, and is very difficult to describe in standard terms because none of its color variations are found in their true tones in the color standards at hand. As the bud begins to unfold, the color becomes lighter, passing progressively through a series of colors which are approximately as follows: *Outer surface of petals*—a combination of Flame Scarlet (Plate I) and Coral Red (Plate XIII); to a color between Carnelian Red (Plate XIV) and Coral Red (Plate XIII) with a touch of Flame Scarlet (Plate II); to Bittersweet Orange (Plate II) with a touch of Carnelian Red (Plate XII). The outer surface of the inner petals is somewhat lighter than that of the outer row of petals. Many of the petals have a streak of yellow up the midrib, this being Light Cadmium (Plate IV) at first and later becoming a little less brilliant. When several days have passed and the blossom is fully open, the outer surface fades somewhat around the edges but for the most part retains the brilliance of the last-named colors. *Inner surface of petals*—lighter and containing more of the orange tones than the outer surface, thus giving the open rose a much lighter effect. The color ranges progressively from Orange Chrome (Plate II); to Orange Chrome with a touch of Carrot Red (Plate XIV) to Light Salmon-Orange (Plate II); to Orange Buff (Plate III) overlaid with a slight amount of Ochraceous-Salmon (Plate XV). On both the inner and outer surfaces these colors all merge into the large aiglet of brilliant yellow which is approximately Light Cadmium (Plate IV). As the blossom begins to die it again takes on darker shades.

*Reproductive organs*

Pistils: Very many; tightly bunched.

*Styles.*—Long, reaching far down inside calyx. Martius Yellow (Plate IV), usually with slight reddish tinge at base of stigmas.

*Stigmas.*—Pinard Yellow (Plate IV).

Stamens: Many; loosely cupped about bunched pistils.

*Filaments.*—Uneven lengths; curved so as to extend somewhat cup-shaped; Carrot Red (Plate XIV) at base, merging into Apricot Yellow (Plate IV) at their tops.

*Anthers.*—Large; Apricot Yellow, edged with Mars Yellow (Plate III).

Ovary: Inclosed in calyx.

The color designations are given as observed in flowers cut in the month of January in my greenhouses in Pennsylvania. It is to be understood that there may be some slight variation because of climate and soil conditions.

Having thus disclosed my discovery, I claim;

A new and distinct variety of hybrid tea rose plant, characterized particularly by its prolific growth; its abundant dark leathery foliage; the retention of the form of its large, shapely blossoms; the slow and even opening of its medium-sized, pointed buds; and the distinctive color combination of its buds and blossoms, substantially as shown and described.

MARTIN SAMTMANN.